Figure 1:
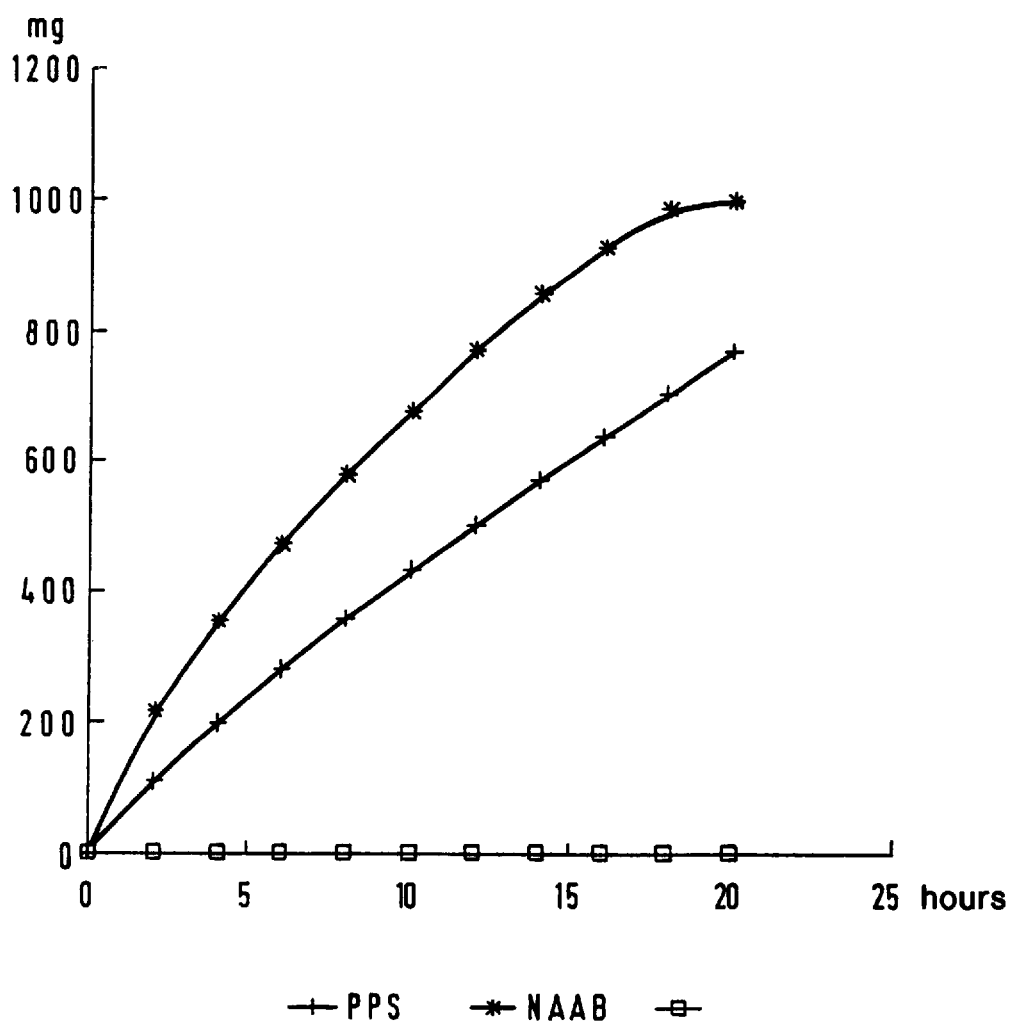

United States Patent
Ehret et al.

[11] Patent Number: 5,830,546
[45] Date of Patent: Nov. 3, 1998

[54] RESERVOIR SYSTEM FOR PROLONGED DIFFUSION OF AN ACTIVE PRINCIPLE

[75] Inventors: Philippe Ehret, Fortschwihr; Christophe Rougeot, Colmar; Hervé Brochard, Wittelsheim; André Stamm, Griesheim, all of France

[73] Assignee: Holvis Holzstoff S.A., Basel, Switzerland

[21] Appl. No.: 955,258

[22] Filed: Oct. 1, 1992

[30] Foreign Application Priority Data

Oct. 3, 1991 [FR] France .................... 91 12186

[51] Int. Cl.$^6$ .............. B65D 83/00; A61K 9/00; A01N 25/34
[52] U.S. Cl. ............ 428/36.1; 206/524.1; 206/484; 220/454; 222/92; 604/408; 604/890.1
[58] Field of Search ............ 424/405; 206/524.1, 206/484; 220/454, DIG. 22; 222/92; 428/35.2, 36.1; 604/408, 890.1

[56] References Cited

U.S. PATENT DOCUMENTS

| | | | |
|---|---|---|---|
| 4,207,893 | 6/1980 | Michaels | 128/260 |
| 4,209,607 | 6/1980 | Shalaby et al. | 528/291 |
| 4,434,153 | 2/1984 | Urquhart et al. | 424/22 |

FOREIGN PATENT DOCUMENTS

| | | |
|---|---|---|
| 0281236 | 9/1988 | European Pat. Off. . |
| 62-246999 | 10/1987 | Japan . |
| 3-038503 | 2/1991 | Japan . |
| 2048710 | 12/1980 | United Kingdom . |

OTHER PUBLICATIONS

Abstract & Partial English Translation of Japanese Patent Publication 1,299,857–A.

Ullmanns Encyklopadie der technischen Chemie, 4th Edition, vol. 21, p. 534 (1982).

Rompp Chemie Lexikon, 9th Edition, vol. 5, pp. 3730–3731 & 4168–4169 (1992).

Ullmann's Encyclopedia of Industrial Chemistry, 5th Edition, vol. A8, pp. 338 & 350 (1987).

*Primary Examiner*—Melvyn I. Marquis
*Assistant Examiner*—Robert H. Harrison
*Attorney, Agent, or Firm*—Wenderoth, Lind & Ponack

[57] ABSTRACT

A reservoir system consisting of a nonwoven made from thermoplastic polymer filaments, shaped into a closed bag containing a water-soluble active principle. The bag is intended to ensure a prolonged release, progressing linearly, of the active principle in an aqueous environment. For a given active principle, the desired diffusion kinetics are obtained by adjusting, depending on the availability of the active principle, the surface area of the nonwoven and the degree of hydrophily of the latter. To this end, it is impregnated, either with polysiloxane or a quaternary ammonium salt, or with a perfluorinated compound or an acrylic resin and paraffin.

6 Claims, 8 Drawing Sheets

RESERVOIR SYSTEM FOR PROLONGED DIFFUSION OF AN ACTIVE PRINCIPLE

The subject of the present invention is a reservoir system for the release and prolonged diffusion of active principles in an environment which is aqueous or subjected to the action of water, and a process for the manufacture of the reservoir system. The new reservoir system makes possible a slow and constant release spread linearly over time and generally lasting for a period of at least a week.

It is made, at least as regards the part intended to be in contact with water, of a nonwoven consisting of continuous monofilaments or/and microfibers made of synthetic thermoplastic polymers and fashioned, or combined with a sheet of an impermeable material, into the shape of a closed bag containing one or more active principles which are soluble in water or which can be rendered soluble in the aqueous environment for which they are intended.

For a given active principle, the desired linear release kinetics are obtained by accordingly adjusting the degree of hydrophily of the nonwoven and the dimensions of the nonwoven which define the surface area for exchange between the internal volume of the reservoir system and the aqueous environment for which it is intended.

The prolonged release and diffusion of active principles in certain environments have already been made the subject of many trials, and solutions of very different kinds have been proposed to achieve them.

Thus, U.S. Pat. No. 4,207,893 describes a tubular device for releasing a fluid containing an active principle. The fluid is contained in a flexible tube whose ends have two small flow openings. This tube is surrounded by a laminate made of an absorbent material and of a polymer which is hydrophilic and capable of swelling. The whole is inserted into a rigid tube made of a permeable or microporous material. When placed in a biological environment, such as a body cavity, the device absorbs water, the hydrophilic polymer swells and thus exerts a pressure on the flexible tube which contains the fluid.

A device of analogous construction, but with a different mode of action, is described in GB 2,048,710. The flexible tube contains, at one of its ends, a capillary channel through which the fluid can flow; the laminate, which is absorbent and can swell, is replaced by a composition of high osmotic activity. When the device is placed in an aqueous environment, such as a body cavity, the composition attracts water by osmosis through the permeable or microporous rigid tube, and the composition thus increases in volume and exerts pressure on the flexible tube containing the fluid.

These devices have a complicated construction, which is reflected in the manufacturing processes and costs. These disadvantages have prompted research into simpler and more economic systems. The solutions commonly adopted are based on the incorporation of the active principle into a polymer substance which acts as a matrix, and its diffusion from this matrix; they differ from each other in the chemical composition of the matrix and in the mode of action of the ambient environment on it.

According to EP 281,236, the matrix is a crosslinked silicone elastomer, within which a polar or hydrophilic liquid phase containing the active principle is dispersed in microcapsules with a diameter of less than 20 micrometers and forms a water-in-oil emulsion, by virtue of a dispersion agent. Where the matrix has a high mechanical strength, it can be used as an implant in a living organism and, in the contrary case, for dermal application of the active principle; the degree of crosslinking inversely influences the rate of release of the active principle.

A matrix of another type is described in U.S. Pat. No. 4,434,153. It consists of a hydrophilic polymer capable of increasing in volume by absorption of water and of disintegrating by hydrolysis or biological erosion. The disintegration of this matrix in the stomach of an animal or a human being releases a multitude of pills with a diameter of approximately 0.5 to 1 cm which contain the active principle. The latter, in the form of a nucleus, is contained in an enclosure consisting of a mixture of a wax and a triglyceride or of some other material capable of controlling the rate of release; the active principle is released by diffusion through the enclosure or by disintegration of the latter, biological erosion or rupturing by osmotic pressure. The delay effect thus results from two superimposed coatings, which disintegrate one after the other.

According to the U.S. Pat. No. 4,209,607, polyester amides are obtained by reaction of bisoxamidodiols with dicarboxylic acids or their diesters, for example oxalic, succinic, suberic or terephthalic diesters. The derivatives of oxalic esters are sensitive to hydrolysis; they can be used for manufacturing absorbable items for surgery, especially threads for suturing. The derivatives of succinic and other esters are resistant to water; they can be used for nonabsorbable surgical sutures and as textile fibers.

Patent JP-A-1,229,857 describes a nonwoven membrane consisting of poly(vinyl alcohol) filaments and of polyolefin, polyamide or polyester fibers which is capable of fixing, by chemical affinity, microorganisms, bacteria, spores, and the like. This membrane can be used in microbiology, especially for the treatment of sewage and of waste water from the manufacture of foodstuffs or enzymes.

It is clear that the above matrix systems would in no way suggest a reservoir system in the form of a closed bag, consisting of a nonwoven permeable to water because of adjustment to a certain degree of hydrophily, as the subject of the invention was defined above.

An essential element of the invention is the prolonged and constant nature of the diffusion of the active principle which the nonwoven has to ensure and which it must maintain during the period of use. If the fact is considered that the reservoir system is intended to be used in an aqueous environment or in an environment in which water can be used as the vehicle for an active principle, it is clear that the diffusion properties must not be modified when the system is subjected to the action of water, which would disturb the linear nature of the release kinetics.

Now, it has been found that it is possible to adjust, on a long-term basis, the degree of hydrophily of a nonwoven to a certain level, selected according to the solubility in water of the intended active principle, by impregnation with certain specific groups of compounds.

In the case of a nonwoven of hydrophobic nature, it turns out that impregnation, either with polysiloxanes or polymers based on polysiloxane, or with quaternary ammonium salts of amphoteric type, will give this nonwoven a permanent hydrophilic nature. These observations are highly surprising. Indeed, polysiloxanes are known as compounds with a hydrophobic nature (Römpp Chemie Lexikon, 9th edition, vol. 5, page 4169, Georg Thieme Verlag, Stuttgart, New York, 1992) and not as hydrophily agents, but nevertheless this is what emerges from the tests presented in the following examples. The fact that hydrophobic fibers or filaments can become wettable, that is to say permeable to water, by the effect of a polysiloxane cannot be explained to date. On the other hand, in view of the hydrophilic nature (ibidem, page 3731) of quaternary ammonium salts, it could have been expected that they are redissolved and removed (leached) from the nonwoven when the reservoir system is subjected to the action of water. Nevertheless, this is not the case, as laboratory tests show: these salts remain fixed, on a long-term basis, to the nonwoven, if impregnation was carried out correctly.

In the case of a nonwoven of hydrophilic nature, that is to say wettable with water, the water of the aqueous medium can freely diffuse through the nonwoven. Release of the active principle will therefore occur in a direct way, at a rate essentially dependent on its solubility in water. It is therefore imperative, if it is desired to obtain a release of the active principle which is slow and constant and spread linearly over time, to reduce, on a long-term basis, the degree of hydrophily of the nonwoven and, for this purpose, to impregnate it with a water-repelling agent. However, such an agent, if it is fixed in a lasting fashion on the fibers or filaments, should make them entirely hydrophobic. Now, it has been found, contrary to all expectations, that perfluorinated compounds and water-repelling agents based on an acrylic resin and paraffin are fixed to the fibers in a lasting fashion but, however, without entirely masking the fundamental hydrophilic nature of the nonwoven.

The invention is described below in more detail. In the appended FIGS. 1 through 5 and 10, the abscissa represents the time, in hours or in days, and the ordinate represents the quantity of active principle released, in mg.

The nonwoven used to manufacture the bags is made according to known processes, generally by application of the microfiber blowing process, called melt-blown, or of the continuous monofilament spinning process, called spun. There is thus obtained either a spun and blown nonwoven or a spun nonwoven.

The nonwoven preferably consists of microfibers or continuous monofilaments made of polyolefins, polyesters or polyamides, especially made of polypropylene, polyethylene, poly(butylene terephthalate) and/or poly (ethylene terephthalate).

By way of example, polypropylene, polyethylene and poly(butylene terephthalate) are highly hydrophobic: nonwoven fabrics made of these polymers are impermeable to water if a hydrophily agent was not used beforehand to make them wettable. Conversely, the majority of the polyamides are very hydrophilic; this is the case for polyhexamethyleneadipamide, among others. They therefore require, in order to be used in the reservoir system according to the invention, a prior treatment with an agent capable of permanently lowering the degree of hydrophily. As for the polyesters, the degree of hydrophily can, depending on their composition, bring them close to either of the groups.

FIG. 1 shows, in the case of a nonwoven fabric made of polypropylene, the influence of the chemical nature of the compound used to give the nonwoven the degree of hydrophily required for release of the active principle. Impregnation was carried out with a 0.01% alcohol solution of polyether polydimethylsiloxane (PPS) and of N-alkylaminobetaine (NAAB), respectively. 1000 g of paracetamol were used as active principle. The standard, a similar fabric but unimpregnated, is represented by the square signs aligned along the abscissa; it shows that there is no release of the active principle.

It is possible to use as polysiloxanes, among others, water-soluble organomodified polysiloxanes and copolymers of polysiloxane and polyether, such as those which are described, for example, in Ullmanns Encyklopädie der technischen Chemie, 4th edition, volume 21, page 534 et seq. (Verlag Chemie GmbH, Weinheim/FRG 1982).

Quaternary ammonium salts of the amphoteric type means quaternary ammonium compounds, one of the alkyl substituents of which carries an acidic (or anionic) group, especially a carboxylic group, a sufonic group, a sulfuric group, a phosphonic group or a phosphoric group. These substances are also called betaines, for example the N-alkylaminobetaines. It is thus possible to use, among others, dialkyldimethylammonium or 1,2-dialkyl-3-methylimidazolinium chlorides or methylsulfates, one alkyl substituent of which carries one of the abovementioned acidic groups. This subject can be referred to in Ullmann's Encyclopedia of Industrial Chemistry, 5th edition, volume A8, page 350 et seq. (VCH Verlagsgesellschaft mbH, Weinheim/FRG 1987).

There will be cited, as specific examples of the two groups of products mentioned above, on the one hand, the polyether-polydimethylsiloxane copolymer Hansa Finish 1601, a nonionic surface-active agent manufactured by H.T.C., Hansa Textilchemie GmbH, Oyten bei Bremen/FRG, and distributed under the trade name Abil B 8851 by Goldschmidt France SA, F-78180 Montigny le Bretonneux. The chemical name of this product is dimethicone polyol, corresponding to the following formula:

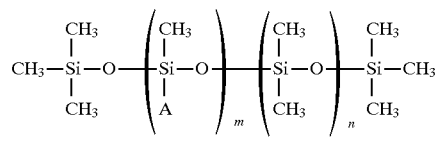

with m=approximately 5, n=approximately 60 and A=(CH$_2$)$_3$—O—(CH$_2$CH$_2$O)$_x$—(CH$_2$CH$_2$CH$_2$O)$_y$H (x and y are undefined).

On the other hand, there will be cited the product KK 71006/1 manufactured by Sandoz Produkte AG, CH-4002 Basle, whose expanded formula is the following:

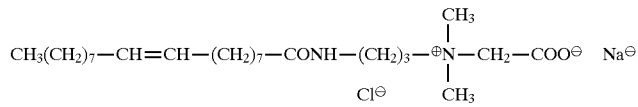

As a specific example of a water-repelling agent, there will be cited the products Paraf fion R$_1$ and Parraf fion R$_2$, manufactured by Röhm GmbH Chemische Fabrik, D-6100 Darmstadt 1 (FRG), both based on an acrylic resin and paraffin but which differ in the degree of their viscosity.

Impregnation of the nonwoven with one of the abovementioned products can be advantageously carried out by treating the nonwoven with a solution of the said product in a suitable solvent, such as water, a lower aliphatic alcohol, diol or polyol, for example methanol, ethanol, isopropanol, ethylene glycol, propylene glycol or diethylene glycol, an ether or a mixture of one of these with water. A suitable method of operating consists in applying the solution by pad mangling or licking and then drying the nonwoven.

Figure 2:
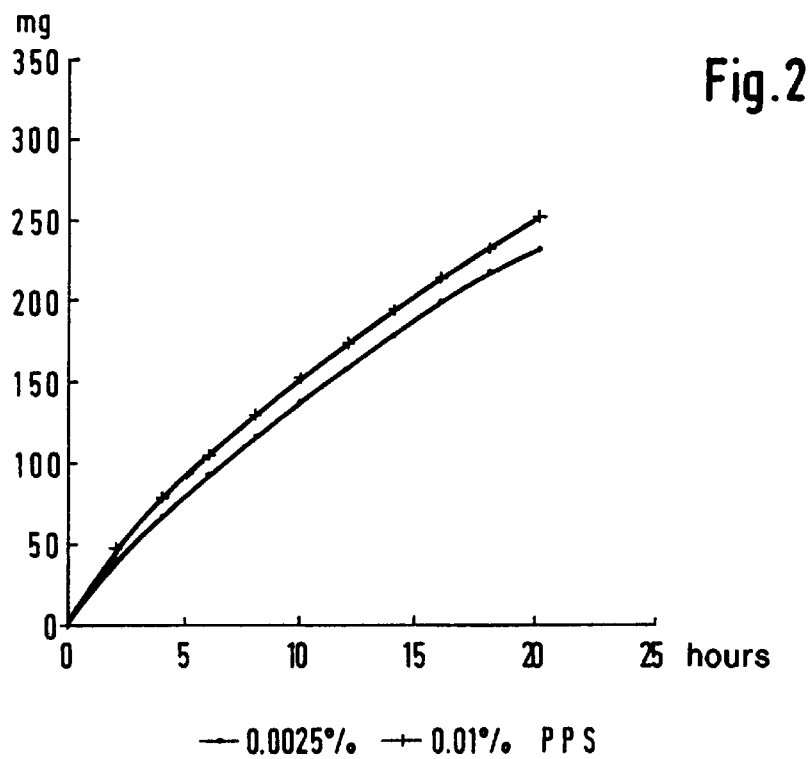
Figure 3:
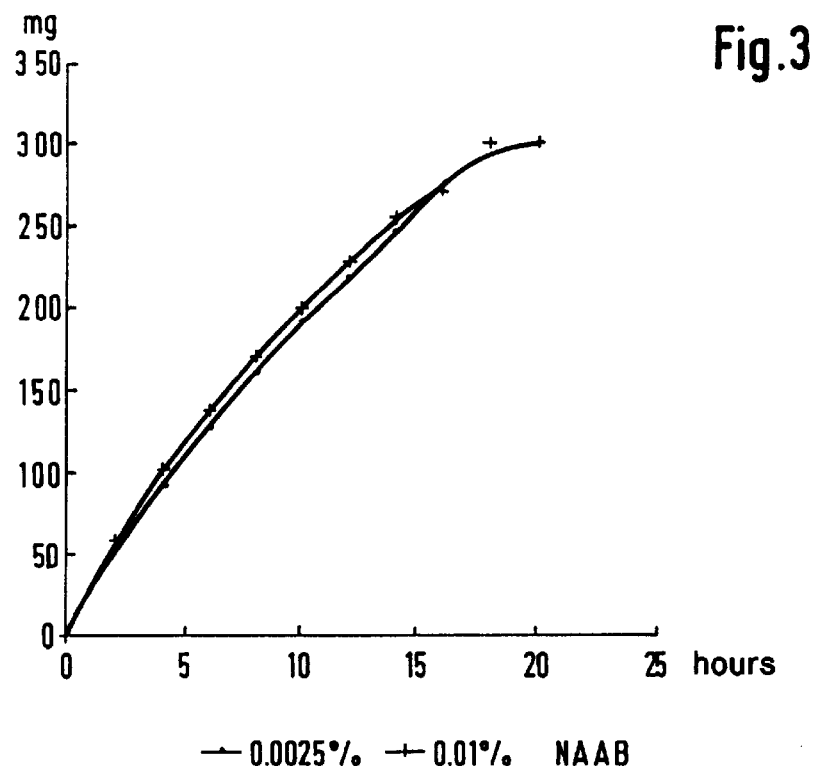

In comparative tests targeted at defining the influence of the concentration of the solution used for impregnation on the release kinetics, alcoholic solutions were used containing 0.0025% and 0.01%, respectively, of a polyether-polydimethylsiloxane (PPS) and of an N-alkyl-aminobetaine (NAAB); the bag of nonwoven was as described in Example 1. Indeed, FIGS. 2 and 3 show no significant difference in the quantities of active principle (sulfadimidine, 300 mg) released after 20 hours. This absence of influence of the concentration confirms that it is indeed the chemical nature and not the quantity of surface agent used which is determining for zero order release kinetics.

After impregnation, it is recommended that the nonwoven be washed with water to remove a fraction of the impregnation agent in excess with respect to the quantity which the nonwoven is capable of fixing, on a long-term basis, and which would delay the establishing of equilibrium conditions in the aqueous environment.

As for the active principle, it is soluble or can be made soluble to a sufficient degree in the environment for which it is intended, that is to say, generally in an aqueous environment such as the rumen of a ruminant or water treatment plants, especially water intended for human requirements. This means plants for the preparing of water for consumption, sanitary fittings, plants for the purification of sewage, those which are used for the preparation of water for swimming pools and public baths, pisciculture ponds, and the like. In addition to the specifically aqueous environments mentioned above, it is also possible to envisage environments which are subjected from time to time to the action of water, in particular soils and culture beds used in horticulture and in arboriculture.

The linear nature of the release kinetics has the well-known effect of excluding concentration fluctuations of the active principle in the aqueous environment, fluctuations which are usually observed when the treatment is carried out by repeated administrations.

Depending on the environment and the purpose which it is proposed to achieve, the active principle can be, in particular, an antibiotic, an antifungal agent, an antiparasitic agent such as an anticoccidial or an anthelmintic, an antiseptic, a vitamin, a trace element, a growth factor, a plant protection product, a fertilizer, an algicide or a combination of two or more of them.

The areas of application are, among others:
veterinary medicine as regards the administration of antibiotics, antiparasitic agents, vitamins and the like, both as preventatives and as curatives. In this case, antiinfectious and antiparasitic agents are intended in particular to avoid the risks of infection during transportation and grazing;
water treatment, such as the controlling of algae, fungi and bacteria;
horticulture and arboriculture, where it is possible to expose a plant or a tree to the effects of a fertilizer or a growth factor without risking damage to the roots or the trunk.

In order to modify the availability of the active principle (s) with respect to the surrounding aqueous environment or subjected to the action of water, the reservoir system can additionally contain one or more excipients and/or additives. These must either promote the availability to the surrounding environment of active principles whose solubility coefficient in water is zero or judged to be insufficient, or restrict the availability to the said environment of active principles whose solubility coefficient is judged to be too high. To this end, there will be used either surface-active agents (see Ullmann's Encyclopedia of Industrial Chemistry, 5th edition, volume A8, page 338 et seq. (VCH Verlagsgesellschaft mbH, Weinheim/FRG 1987) or swelling agents which form gel matrices which delay diffusion of the active principle(s) in the surrounding environment (polyacrylates, starch modified by grafting, and the like). An example of the said polyacrylates is the product Favor SAB manufactured by Stockhausen France, F-60100 Creil; it is a salt of a crosslinked and grafted copolymer of poly(acrylic acid) and a polyol.

Other excipients and/or additives make it possible, for example, to accelerate the process of diffusion of water from the surrounding environment towards the interior of the reservoir system; these are, for example, salts possessing an osmotic power, especially sodium chloride.

The reservoir system can also contain a grid consisting of a biodegradable semisynthetic polymer and which confers a sterical hindrance on it such that, placed in the rumen of a ruminant, it cannot be regurgitated.

Figure 4:
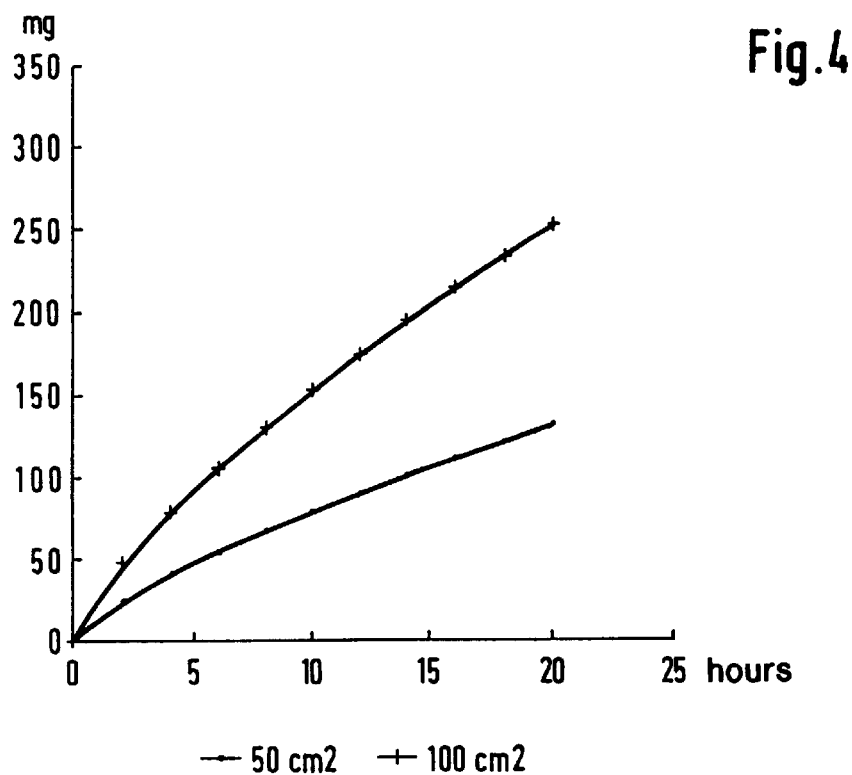

Moreover, the rate of release increases as the surface area for exchange between the medium to which the reservoir system is subjected and the inside of the sachet increases, as emerges from FIG. 4. The quantities of sulfadimidine released after 20 hours by reservoir systems charged at 300 mg and having surface areas for diffusion of 50 and 100 cm$^2$ were, respectively, 131±9 mg and 252±18 mg. It is seen that, when the surface area for diffusion doubles, the quantity of active principle released increases in approximately equal proportions (1.93 times).

Figure 5:
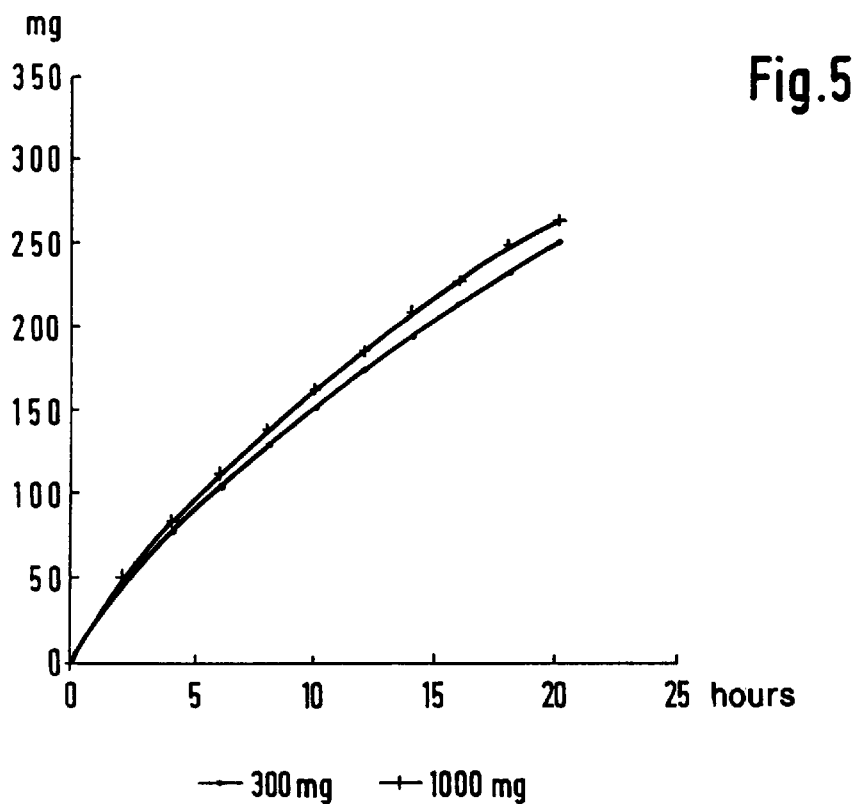

The charge of active principle has, all other parameters staying the same, no influence on the release kinetics, as long as the inside of the reservoir system is kept saturated with active principle. FIG. 5, for sulfadimidine charges of 300 mg and 1000 mg respectively, shows substantially the same curve.

The duration of effect of the system therefore depends on the surface area for exchange of the bag and on the quantity of active principle incorporated in the bag.

The mechanisms governing the diffusion of the active principle in the proposed model are closely related to Fick's law. This makes it possible to explain in particular the linear nature of the release kinetics and to fix the limits thereof by applying the following modification of Fick's law:

$$\text{modification of Fick's law: } \frac{dq}{dt} = -D \times S \times \frac{dc}{dx}$$

$\frac{dq}{dt}$ = diffusion rate $D$ = diffusion coefficient (function of the coefficient of solubility of the active principle and of the intensity of the hydrophilic treatment)

$S$ = surface area for exchange $\frac{dc}{dx}$ = concentration gradient between the internal and surrounding environments The linear nature of the rate of release of the active principle is only effective if the difference in concentration of the active principle between the aqueous environment to which the reservoir system is subjected and the environment consisting of the inside of the system is constant.

Thus the undissolved fraction of the active principle replaces, during the diffusion, the dissolved part of the active principle which is released. The concentration of active principle inside the bag will therefore be maintained at saturation until the undissolved fraction of the active principle is exhausted, that is to say during the whole period of effect of the system.

It is therefore advisable to define the charge of active principle to be introduced into the bag during manufacture as a function of the rate of diffusion of the active principle, of the duration of desired effects, and of the surface area for exchange of the reservoir system.

An applied process for manufacturing and filling the reservoir system with active principle is characterized in that, from one or two strips of a nonwoven consisting of microfibers or continuous monofilaments made of thermoplastic synthetic polymers and adjusted to a degree of hydrophilicity defined as described above, a bag of rectangular or square shape i pepared, the width of the strip or the two strips determining the width of the bag, either by folding a strip in two, or by superimposing two strips one on the other, in both cases in the longitudinal direction so that the edges lie over each other, either one over the other in the case of folding or in twos in the case of superimposing; in the latter case both the edges are welded on one of the sides, in both cases weldings are then carried out in the transverse directions, at equal distances, the distance between two transverse weldings determining the length of the bag, the active principle(s) and, if appropriate, the excipient(s) or/and additive(s) are introduced into the bags through the side which remains open between two transverse welds, by means of a dosimeter, the edges on the side which remains open are welded together, in order to close the bags, and they are separated from each other by cutting along the transverse welds.

The weldings are advantageously carried out by the action of heat or ultrasound or by bonding. The dosimeter can be, in particular, a metering pump or any other machine for filling and packaging sachets used in the food industry. Manufacture will be carried out, for example, in a workshop which observes the directions known under the name of "Good Manufacturing Practice".

The reservoir systems obtained are preferably stored in a dry environment, advantageously in cardboard or polyethylene containers.

Dissolution Tests

The in vitro dissolution tests were carried in the Laboratoire de Pharmacotechnie of the Faculty of Pharmacy at the University of Strasburg on an automatic dissolution system comprising:

- a dissolution apparatus equipped with an automatic sampling system
- a spectrophotometer for the UV-visible region
- a computer with its accessories, provided with software making possible a direct. integration and interpretation, especially statistical, of the results.

Procedure

In accordance with the second edition of the Pharmacopée Européenne, vol. 5, chapter 4: (July 1987), test entitled "Dissolution test on solid oral forms" according to the method called the rotating paddle method.

Dissolution medium: distilled water

Volume: 1000 ml

Rate of rotation of the paddles: 25 revolutions/min.

Sachets fixed to the paddles of the dissolution apparatus

Spectrophotometric determination: the wavelength selected depends on the active principle introduced Duration of the test: variable FIGS. 6 through 10 illustrate the prolonged nature of the diffusion of the active principles in vitro from a reservoir system in accordance with the present invention. The abscissae represents the time (t) expressed in hours in FIGS. 6, 8 and 9 and in days in FIGS. 7 and 10; the ordinates represent, in FIGS. 6 through 9, the percentage of the initial quantity of active principle released in time t (%, mass/mass) and, in FIG. 10, the quantity released per day, in mg.

Figure 6:
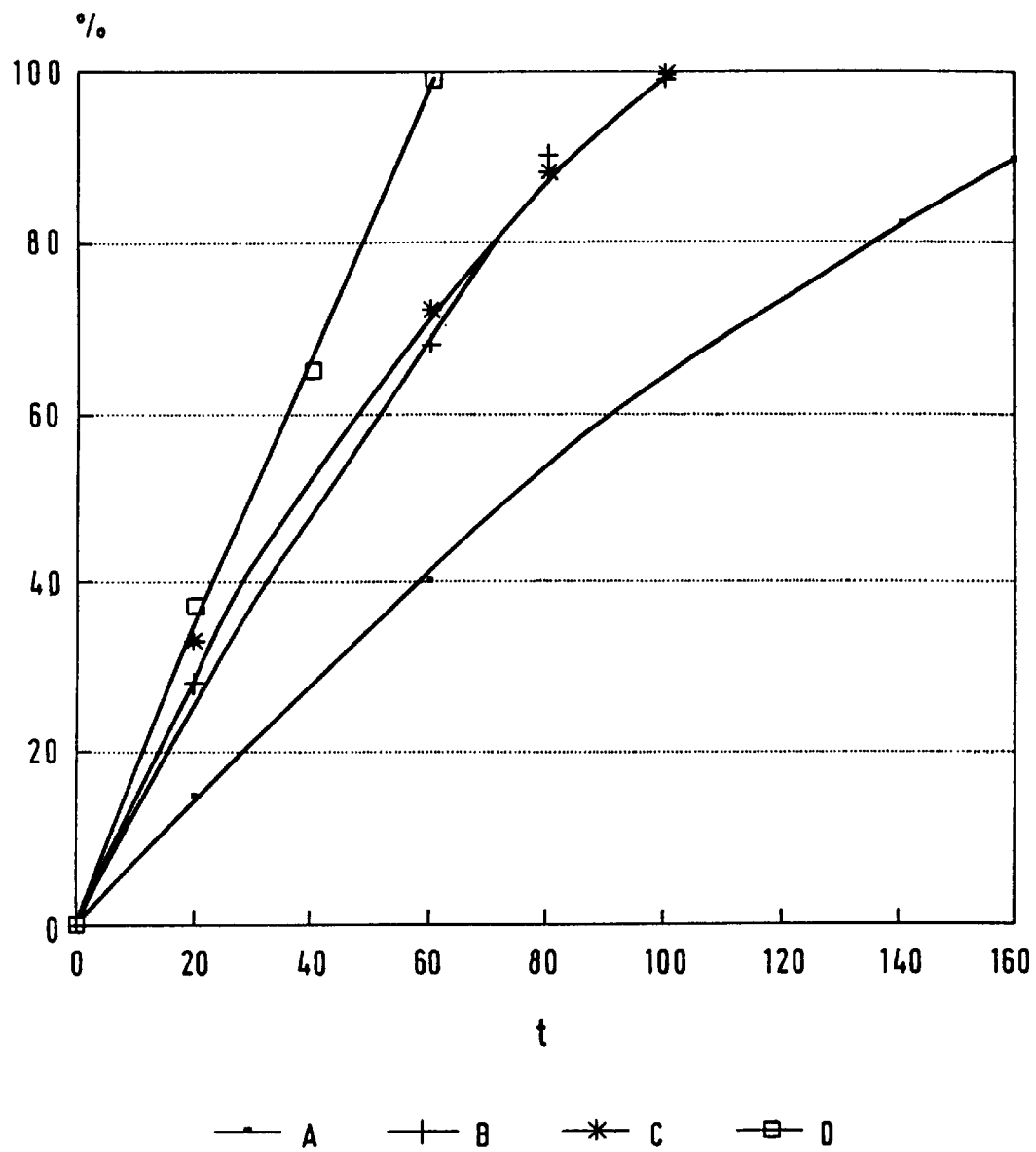
Figure 7:
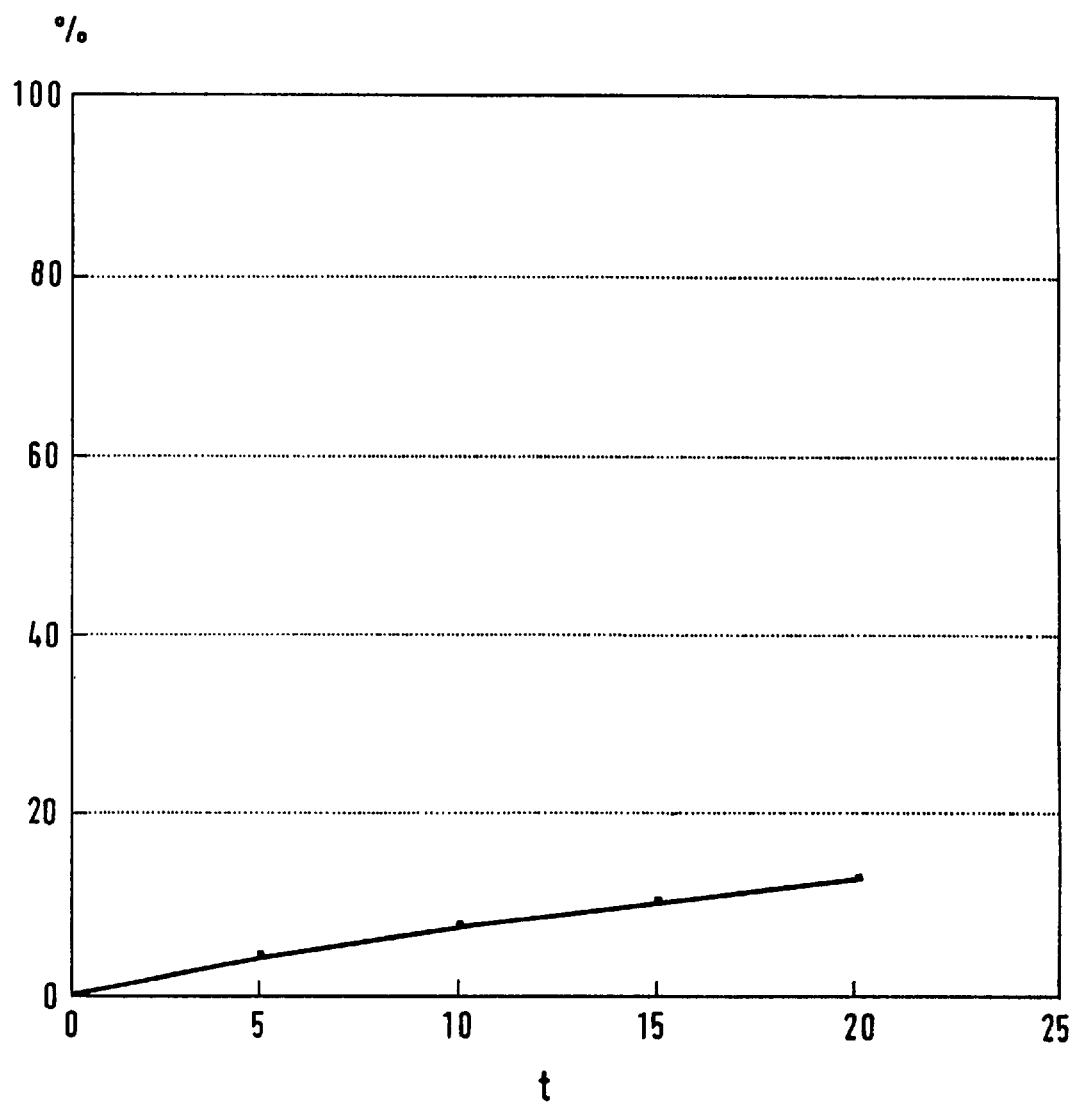
Figure 8:
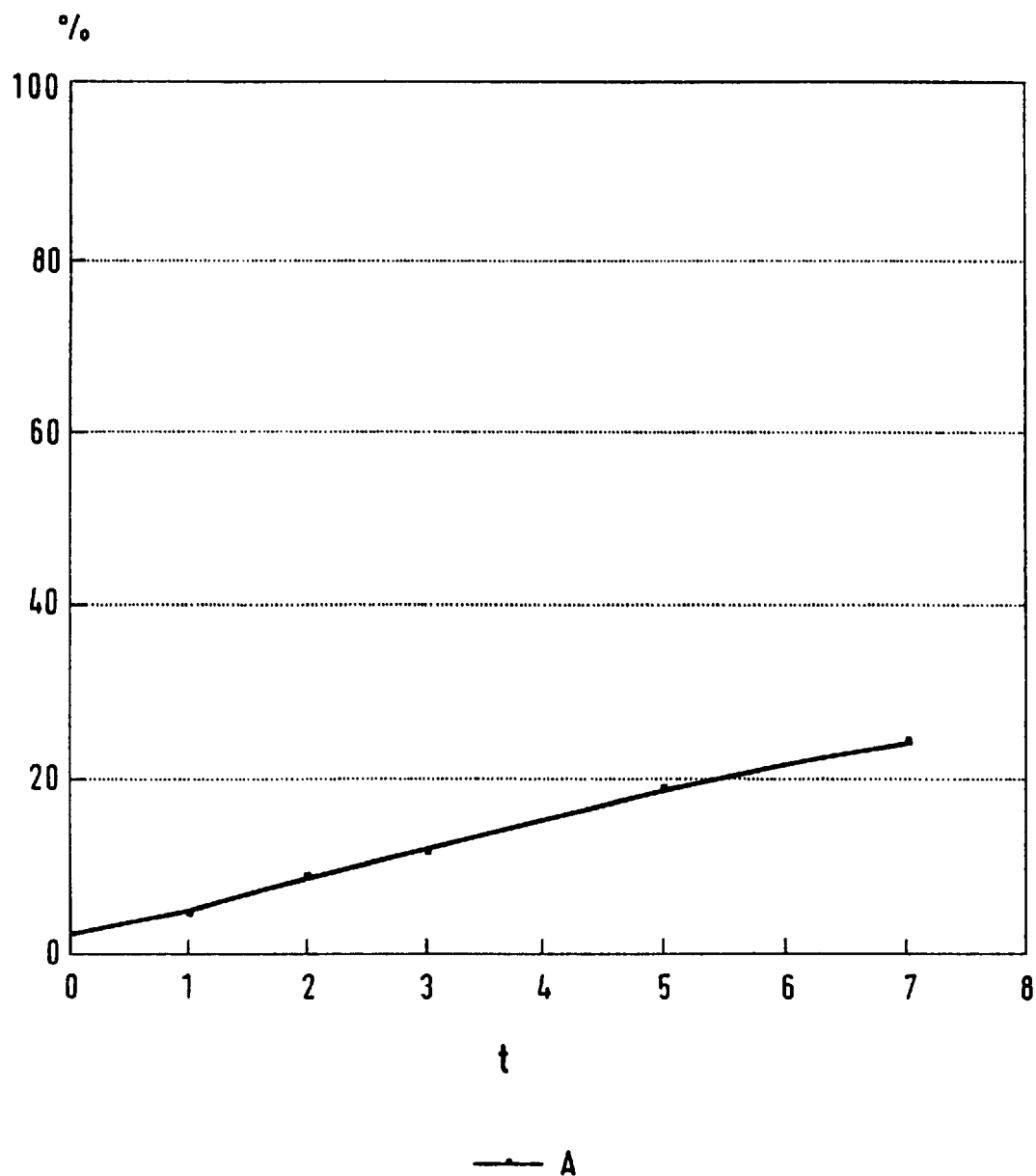
Figure 9:
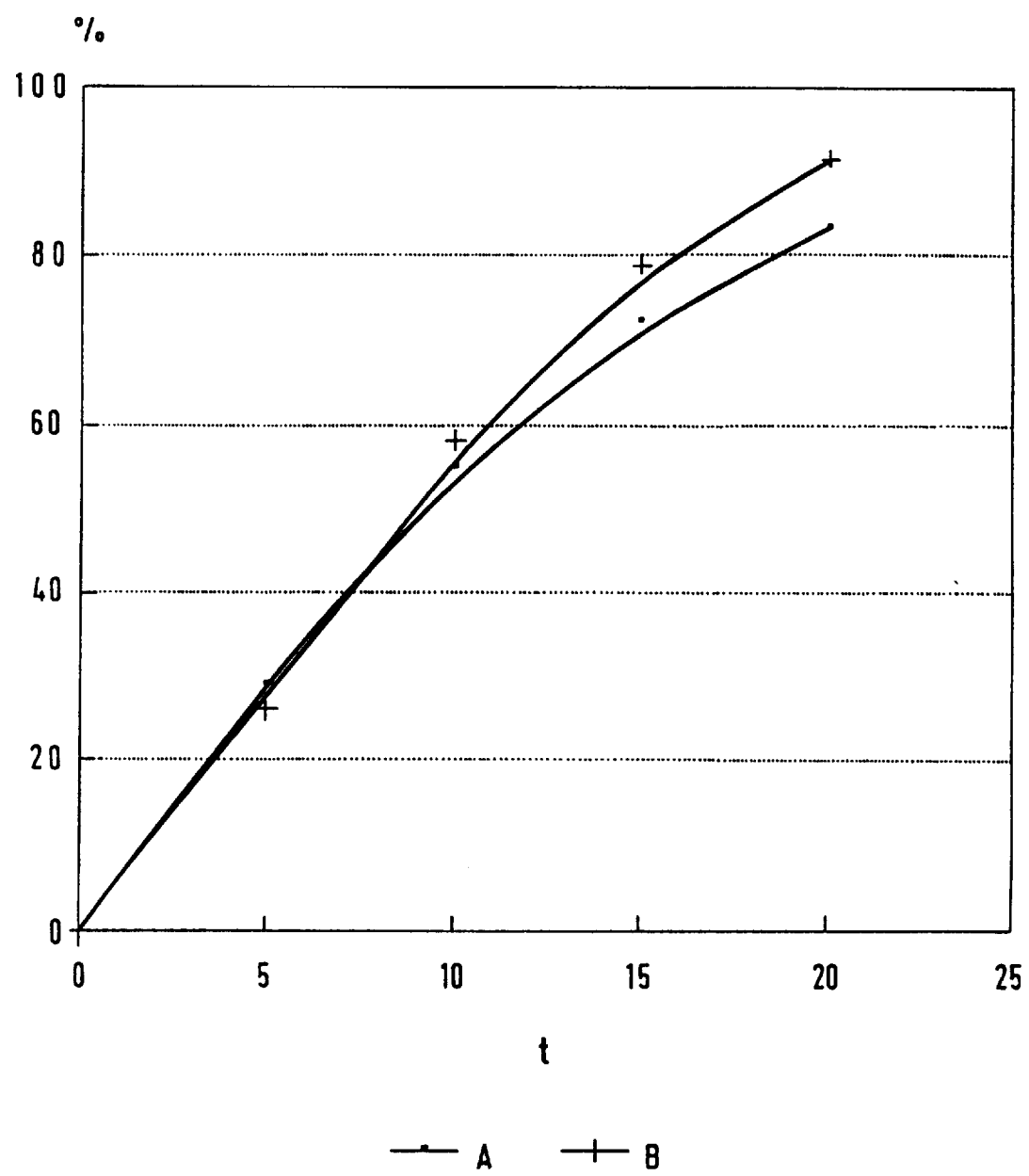

FIGS. 6 through 9 represent the release kinetics of sulfadimidine—FIGS. 6 and 7—and paracetamol—FIGS. 8 and 9—from reservoir systems whose characteristics are described in Examples 1 through 4 respectively.

EXAMPLE 1

Bags of 10×10 cm size are made from a 100% polypropylene nonwoven obtained by the so-called melt-blown process. The characteristics of the polypropylene are the following:

weight per square meter: 20 g/m$^2$ strength, machine direction: 6.6 N/inch transverse direction: 2.9 N/inch extension, machine direction: 21.2 % transverse direction: 53.3% water absorption: 605%.

This ability to fix water is obtained by impregnating the polypropylene using an ethanolic solution of Hansa Finish 1601, an organomodified polysiloxane from the Company H.T.C., Hansa Textilchemie GmbH; no mention of hydrophilic treatment is made by the manufacturer. Once the nonwoven is impregnated by licking (speed of the coating roller: 8.8 m/min., speed of travel of the nonwoven over the coating roller: 15 m/min.), it is dried and fashioned as described above.

0.5 g of sulfadimidine, weighed exactly, are introduced inside each bag. The whole is then subjected to the above-mentioned solution test.

The concentration of the ethanolic solution of Hansa Finish 1601 is, expressed in percent (mass/volume):

for batch A=0.5% for batch B=1.0% for batch C=1.5% for batch D=1.0%.

FIG. 6 shows that:

batch D releases 100% of 0.5 g=0.5 g of sulfadimidine after 60 hours batches B and C release 100% of 0.5 g of sulfadimidine after 98 hours batch A releases 90% of 0.5 g=0.45 g of sulfadimidine after 160 hours.

For all 4 batches, the diffusion kinetics of sulfadimidine have a prolonged and linear nature.

EXAMPLE 2

Reservoir systems with a 7×7 cm size are prepared by hot joining two nonwoven fabrics by passing through a calender:

a) a 100% polypropylene nonwoven fabric obtained by the so-called melt-blown process:
   weight per square meter: 20 g/m$^2$
   made hydrophilic by a 0.01% ethanolic Hansa Finish 1601 solution.

The procedure is identical to that of Example 1.

b) a 100% polypropylene nonwoven fabric obtained by the so-called spun process:
   weight per square meter: 70 g/m$^2$
   made hydrophilic by a 1% ethanolic Hansa Finish 1601 solution.

The procedure is identical to that of Example 1.

The nonwoven fabric described in a) provides the properties of prolonged diffusion of the active principle and the nonwoven fabric described in b) provides the mechanical strength properties of the reservoir system.

5.0 g of sulfadimidine are introduced into each reservoir system of batch A (see Example 1).

FIG. 7 shows that batch A released 13% of 5.0 g=650 mg of sulfadimidine after 20 days, the diffusion kinetics having a prolonged and linear nature.

EXAMPLE 3

The characteristics of the reservoir systems prepared are exactly the same as those of the reservoir systems described in Example 2. On the other hand, the active principle studied is different: 1.0 g of paracetamol is introduced into each reservoir system of batch A.

FIG. 8 shows that batch A releases 24% of 1.0 g=240 mg of paracetamol in 7 hours, the diffusion kinetics having a prolonged and linear nature.

EXAMPLE 4

1) Batch A

Reservoir systems of 7×7 cm are prepared by hot joining of two monwoven [sic] fabrics by passing through a calender:
- a) a 100% polyethylene nonwoven fabric obtained by the so-called melt-blown process:
  weight per square meter: 20 g/m$^2$
  treated hydrophilically with a 0.01% ethanolic Hansa Finish 1601 solution.
  The procedure is identical to that of Example 1.
- b) a nonwoven fabric identical to that described in Example 2, b).

2) Batch B

Reservoir systems of the same size are prepared by hot joining of two nonwoven fabrics by passing through a calender:
- a) a 100% poly(butylene terephthalate) nonwoven fabric obtained by the so-called melt-blown process:
  weight per square meter: 20 g/m$^2$
  not treated hydrophilically.
- b) a nonwoven fabric identical to that described in Example 2, b).

1.0 g of paracetamol is introduced into each of the reservoir systems of batches A and B.

FIG. 9 shows that batch A releases 83% of 1.0 g=830 mg of paracetamol in 20 hours and that batch B releases 92% of 1.0 g=920 mg of paracetamol in 20 hours, the diffusion kinetics having a prolonged and linear nature for both batches.

EXAMPLE 5

A square 10×10 cm sachet is prepared from a 70 g/m$^2$ fabric consisting of polypropylene filaments with a diameter of 30 μm, intended to form the outer wall of the sachet, and from a 20 g/m$^2$ fabric consisting of polypropylene filaments with a diameter of 3 μm, intended to form the inner wall. The latter is treated by licking with a 0.01% alcoholic N-alkylaminobetaine (NAAB) solution. After this treatment, the two fabrics are hot-joined by passing them through a calender, but ensuring that welding of the respective edges is not carried out on one of the sides of the sachet. A polyethylene grid containing 5 mm mesh openings and then the active principle, namely 1000 mg of paracetamol, are introduced into the sachet through the side which has remained open. After welding the side which has remained open, the sachet is subjected to the disolution test described above. The release kinetics are illustrated by FIG. 1.

EXAMPLE 6

Figure 10:
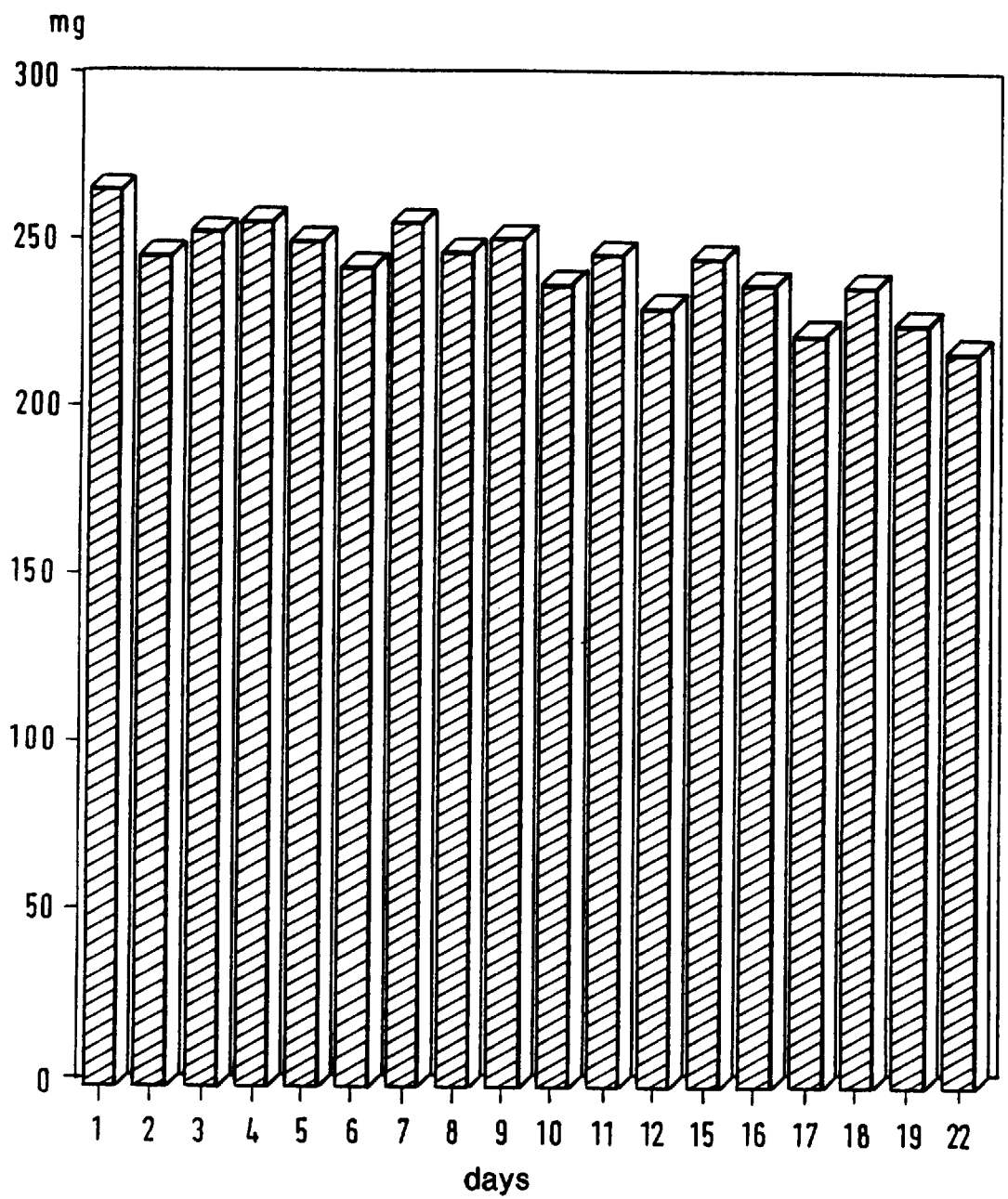

FIG. 10 represents the quantity of sulfamethazine released each day, for a period of time of 22 days, from a bag made of polypropylene nonwoven, with a surface area of 100 cm$^2$ (reinforced with a nonwoven fabric of the same surface area, such as described in Example 2b), containing 10 g of sulfamethazine and treated beforehand with a copolymer of polyether and polydimethylsiloxane. The release of the active principle follows zero order kinetics at the rate of 245±13 mg (n=5) per day for 22 days ($R^2$=0.9995). The quantity released each day is sufficient to prevent coccidiosis in lambs.

We claim:

1. Reservoir system for prolonged and constant diffusion, in an environment which is aqueous or subjected to the action of water, of an active principle which is soluble or which can be made soluble in the said environment, characterized in that it is made, at least in part, of a nonwoven consisting of continuous monofilaments or/and of microfibers made of thermoplastic synthetic polymers, the said nonwoven being (a) treated either, if it is hydrophobic in nature, with a polysiloxane or a polymer based on polysiloxane or with a quaternary ammonium salt of amphoteric type, or, if it is hydrophilic in nature, with a perfluorinated compound or with a water-repelling agent based on an acrylic resin and paraffin, and (b) fashioned, or combined with a sheet of an impermeable material, into the shape of a closed bag containing the active principle, and in that, for a given active principle, the degree of hydrophily conferred or left on the nonwoven and the dimensions of the nonwoven which define the surface area for exchange between the internal volume and the aqueous environment for which it is intended are variable and adjusted for the desired linear release kinetics.

2. Reservoir system according to claim 1, characterized in that the nonwoven consists of a member selected from the group consisting of microfibers and monofilaments made of a member selected from the group consisting of polyolefins, polyesters and polyamides.

3. Reservoir system according to claim 2, characterized in that the nonwoven consists of a member selected from the group consisting of microfibers and monofilaments made of a member selected from the group consisting of polypropylene, polyethylene, poly(butylene terephthalate) and poly(ethylene terephthalate).

4. Reservoir system according to claim 3, characterized in that the nonwoven consists of a member selected from the group consisting of microfibers and monofilaments made of polypropylene.

5. Reservoir system according to claim 1, characterized in that the active principle is combined with one or more members selected from the group consisting of excipients and additives making it possible to adjust its availability with respect to the aqueous environment for which it is intended.

6. Reservoir system according to claim 1, characterized in that the active principle is a member selected from the group consisting of an antibiotic, an antifungal agent, an antiparasitic agent, an antiseptic, a vitamin, a trace element, a growth factor, a plant protection product, a fertilizer, an algicide and a combination of two or more of them.

* * * * *